Figure 1:
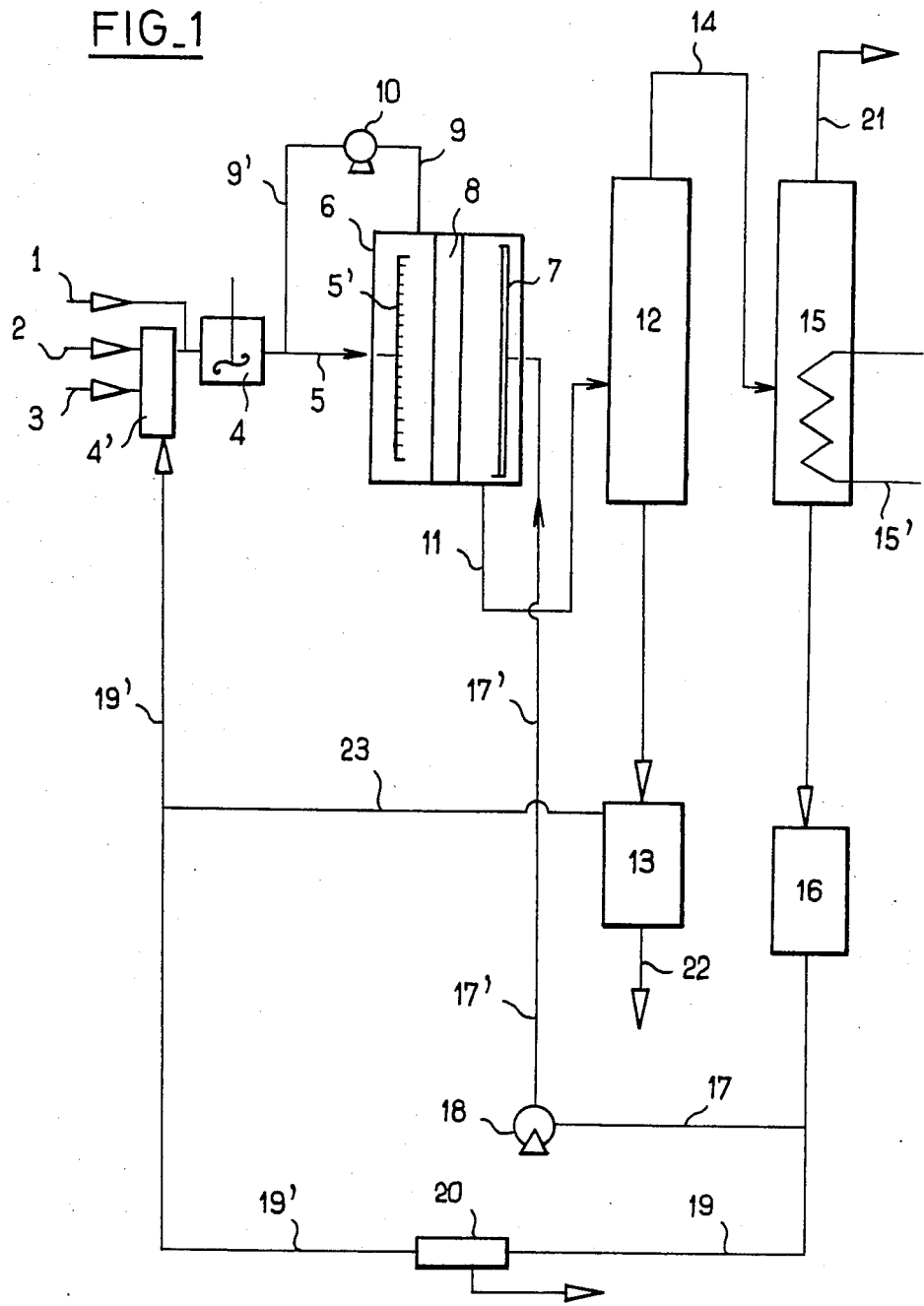

United States Patent [19]
Ollivier et al.

[11] Patent Number: 4,735,747
[45] Date of Patent: Apr. 5, 1988

[54] PROCESS AND APPARATUS FOR THE PHOTOCHEMICAL SULPHOCHLORINATION OF GASEOUS ALKANES

[75] Inventors: Jean Ollivier, Arudy; Hubert Baptiste, Lescar; Christian Lagaude; Michele Larrouy, both of Pau, all of France

[73] Assignee: Societe Nationale Elf Aquitaine (Production), France

[21] Appl. No.: 838,674

[22] Filed: Mar. 12, 1986

[30] Foreign Application Priority Data

Mar. 14, 1985 [FR] France .................... 85 03744
Mar. 3, 1986 [FR] France .................... 86 02910

[51] Int. Cl.$^4$ ............................ C07C 143/00
[52] U.S. Cl. ................................. 260/543 R
[58] Field of Search ...................... 260/543 R

[56] References Cited

U.S. PATENT DOCUMENTS 2,333,788  11/1943  Holbrook et al. ............ 260/543 R Primary Examiner—Paul J. Killos
Attorney, Agent, or Firm—Ostrolenk, Faber, Gerb & Soffen

[57] ABSTRACT

Process of preparation of sulphonyl alkane halides by the reaction between an alkane, sulphur dioxide and a halogen, in the presence of ultraviolet light in the gaseous phase; the gaseous mixture of the reactants contains at least 4 moles of $SO_2$ per mole of hydrocarbon.

13 Claims, 2 Drawing Sheets

PROCESS AND APPARATUS FOR THE PHOTOCHEMICAL SULPHOCHLORINATION OF GASEOUS ALKANES

The present invention relates to the photochemical preparation of alkane sulphochlorides; it is concerned more particularly with the syntheses of such compounds starting with gaseous alkanes at ambient temperature. The invention also comprises an apparatus for carrying out this synthesis.

Because of the industrial utility of sulphonyl alkane chlorides, the preparation of these substances has given rise to the use of several processes in the past. The direct action of $SO_2$ and $Cl_2$ on an alkane under the effect of ultraviolet leads to the production of sulphochlorides, but it gives poor yields mainly because of the formation of large proportions of sulphuryl chloride. As the reaction requires removal of the heat of formation of the desired compound, it is considered practical to operate in a solvent. Thus the standard process consists in bubbling the gaseous mixture of the hydrocarbon, chlorine and sulphurous anhydride into a solvent and more particularly into carbon tetrachloride, the reaction medium being irradiated with ultraviolet light. In this process, which is described in the work by F. ASINGER "Paraffins, Chemistry and Technology" (Pergamon Press 1968) p. 520 et seq., the solvent dissolves the sulphochloride formed, the heat of reaction being removed by a cooling circuit immersed in the reaction medium. However, in order that reaction in a solvent should give good results, it is necessary for it to dissolve readily the hydrocarbon to be treated; it is difficult to find such a solvent and the one which is best industrially, $CCl_4$, also readily dissolves butanes and propanes, but ethane less well and methane poorly, even under a pressure of 8 bars, as can be seen from page 526 of the cited work. In fact, the standard process of sulphochlorination indicated above does not give satisfactory results with methane and its yields are low in the case of ethane.

An important advance was effected in the photochemical process of sulphochlorination by the use of a dispersed liquid phase, constituted by an inert liquid, in practice not dissolving the reactants, but serving as a contact medium between them. Such a process is described in FR No. 2246520, which recommends sulphuric acid as the inert liquid. This process allows the heat of reaction to be conveniently eliminated and gives good results with methane; however, it involves operation on very large amounts of liquid of the order of 2 to 3,000 times the production of the sulphonyl methane chloride.

The present invention adds to the known technique the advantage of not requiring the introduction of any extraneous product into the reaction medium and of forming the latter solely with the required constituents, that is the hydrocarbon, $SO_2$ and halogen, the reaction taking place in the gaseous phase. The process according to the invention allows the production with very good conversions and satisfactory yields both as to the hydrocarbon and as to the halogen. Also, the new process takes place with improved quantitative yields, because it contributes to a better absorption of photons by the halogen, while the heat of reaction is very easily eliminated, avoiding any heating of the gaseous reaction medium.

The new process can be applied well to all gaseous alkanes at ambient temperature and these advantages are shown more particularly in the case of methane, the alkane which is most difficult to sulphochlorinate according to the prior technique.

The process according to the invention, which consists in reacting an alkane with $SO_2$ and a halogen, at a moderate temperature in the presence of ultraviolet light, is characterised in that the mixture contains a large excess of $SO_2$ with respect to the hydrocarbon and also that liquid $SO_2$ is injected into the reaction medium in order to maintain constant temperature.

In the most preferred embodiment, the new process is carried out under pressure, such that the reaction medium remains in the gaseous state, only the sulphonyl alkane halide undergoing liquifaction.

The process thus defined applies to all gaseous alkanes at the temperature chosen for the reaction and to all the halogens; however, as methane sulphochloride is very important industrially, the following part of the present description relates to this substance.

In carrying out the process according to the invention, the preferred proportions of the reactants in the gaseous mixture subjected to ultraviolet radiation preferably vary between the following limits:

| per mole of $CH_4$ | per mole of $C_2$ or higher alkane |
|---|---|
| 4 to 8 moles $SO_2$ | 7 to 14 |
| 0.4 to 1 mole $Cl_2$ | 0.6 to 1 |
| and preferably | |
| 5 to 7 moles $SO_2$ | 10 to 13 |
| 0.7 to 0.9 mole $Cl_2$ | 0.7 to 0.9 |

These ratios are also valid for other halogens.

The process can be conducted at temperatures of about 10° to 90° C. with a preferential range from 30° to 70° C. In the case of methane, it is particularly advantageous to operate between about 50° and 70° C. and most preferably between 55° and 65° C. In the case of ethane and higher hydrocarbons, lower temperatures are preferable, for example 30° to 40° C. for ethane. As already indicated above, the desired temperature is regulated by the injection of liquid $SO_2$ into the gaseous phase in the reactor.

The most advantageous embodiment of the new process uses a pressure, above atmospheric pressure, of 0.1 to 30 bars in the reacting gaseous phase and particularly from 8 to 15 bars. It will be understood that this pressure is calculated as a function of the temperature and of the composition of the reaction mixture, so that it remains gaseous.

Since the photosulphochlorination of alkanes is known per se and it is common practice to employ a mercury vapour lamp for the production of the ultraviolet radiation utilised, it is not necessary to describe this technique here.

The process according to the invention can be carried out in an apparatus of known type, but this should include certain features which are indicated in the accompanying drawings and in the description which follows.

FIG. 1 shows diagrammatically an assembly of apparatus for the production of sulphochlorinated alkanes according to the process of the invention.

In the drawing, the inputs 1, 2 and 3 are respectively those of methane, sulphur dioxide and chlorine, all gaseous, which are introduced into a mixer 4 provided with an agitator to homogenise the gaseous mixture. Preferably, a premixer for the $Cl_2$ with $SO_2$ (references 2 and 3) as indicated at 4', is also provided for safety reasons. By the line 5, the gaseous mixture passes from the mixer 4 into the reactor 6, in which it is distributed uniformly by means of the perforated baffle 5'. Another similar baffle 7 is also placed in the upright direction of the reactor to serve for the introduction of liquid $SO_2$ intended for regulation of the temperature. The reactor is traversed in known manner by an ultraviolet lamp 8. From the top of the reactor 7 a line 9 leaves towards a pump 10, to allow recycling of a fraction of the effluent from the reactor to the line 5, and for predilution of the reactants arriving from 4. The pipe 11 leads the liquid product formed in the reactor 6 to the separator 12, where the liquid phase, that is the crude sulphonyl alkane halide, falls into the intermediate receptacle 13, while the residual gases pass via the conduit 14 into the second separator 15; this separator is provided if required with a condensor 15' for converting the $SO_2$ introduced to the liquid state; liquid $SO_2$ containing $Cl_2$ is recycled after recovery in an intermediate receptacle 16; recycling of the liquid $SO_2$ takes place via 17, by means of the pump 18 and the duct 17' discharging at the baffle 7 into the reactor 6. Another fraction of $SO_2$ derived from 16 passes via the duct 19 into the evaporator 20 and leaves it via 19' to be fed into the mixer 4'. From the top of the separator 15, HCl is evacuated via the conduit 21 to pass to treatment apparatus, not shown. From the bottom of the intermediate receptacle 13, a conduit 22 passes to purification apparatus for the sulphonyl alkane halide produced which as it does not form part of the invention is not shown here.

The principal characteristic which distinguishes the apparatus according to the invention from those of the prior art resides in that the means 7 for the distribution of liquid $SO_2$ are placed in the reactor 6 parallel to the ultraviolet lamp 8. Such means which in practice comprise a perforated baffle can be much more easily located in the reactor than condensors immersed in the liquid phase of a reactor, according to the prior art. Also, the heat exchange by direct contact of the $SO_2$ with the gaseous mixture is much more efficient than exchange through the walls of a tubular bundle or a cooling coil immersed in the reaction medium, according to the prior art.

Another characteristic of the apparatus according to the invention is a mixer 4, where the mixture of gaseous reactants is prepared for reaction in the enclosure 6. In an improved apparatus, a first mixer 4' serves to mix $Cl_2$ with $SO_2$ and the premixture so formed meets the hydrocarbon in 4. According to a preferred feature, an inlet 9' is connected to the passageway 5 to deliver a fraction of the gas derived from the reactor 6, which also constitutes a novel feature of the apparatus.

While any installation of this type necessarily comprises a separator 12, which receives the liquid formed in the reactor, the apparatus according to the invention also has a novel feature in that it comprises a second separator 15 functioning at such temperature that the liquid $SO_2$ flows into the intermediate receptacle 16 in order to be passed from there via the injection means 7 into the reactor 6. At the top of the separator 15, practically all the hydracid formed is discharged via 21 to the appropriate units.

Figure 2:
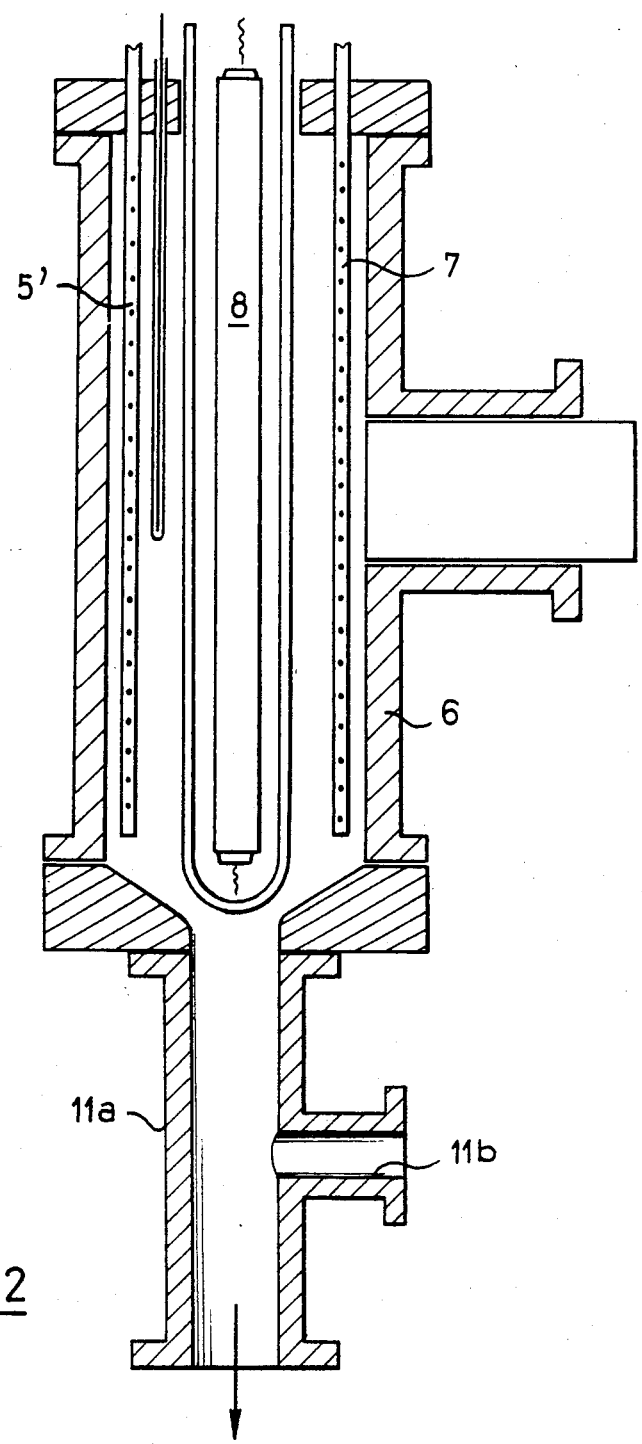

FIG. 2 shows in axial section the reactor 6 equipped with a baffle 5' for the distribution of the reaction mixture, a baffle 7 for the injection of liquid $SO_2$ and an ultraviolet lamp 8. In place of an outlet 11 to the first separator 12, as in FIG. 1, a vertical outlet 11a is provided, leading the liquid from the base of the reactor directly to the intermediate receptacle 13, while a branch line 11b is connected to the separator 12. A column of sufficient height between 11b and 13 is sufficient for the liquid sulphonyl alkane halide produced in 6 to flow regularly from 11a to 13 and for the gases to pass via 11b to 12.

In operating the apparatus according to the invention, the methane arrives via 1, the sulphur dioxide via 2 and the chlorine via 3. These gases are mixed in 4' and 4 and are passed via 5 into the reactor 6. Preferably, a fraction of the gas in the reactor 6 is introduced via 9, 10, 9' into the gaseous stream passing through 5, which gives a preliminary dilution of the gaseous mixture. These reactants are distributed throughout the height of the reactor by means of a baffle 5' which produces homogeneous diffusion in the reactor.

The mercury lamp 8 is lit and the temperature of the interior of the reactor is regulated to the desired value by the injection of liquid $SO_2$ by means of the baffle 7, the reaction taking place and the sulphonyl alkane halide produced flowing from the bottom of the reactor via 11, in order to be passed into the separator 12.

The liquid phase which flows from the separator 12 to the intermediate receptacle 13 is constituted by the crude sulphonyl alkane halide; it can thus contain certain amounts of secondary products, particularly methylene dichloride, $CH_2Cl_2$, chloroform, $CHCl_3$, carbontetrachloride, $CCl_4$, hexachloroethane, $C_2Cl_6$, and dimethyl disulphone $CH_3SO_2SO_2CH_3$. The process according to the invention allows very small amounts of these impurities to be produced but nevertheless purification by distillation can be carried out in known manner and takes place in a circuit to which the duct 22 leads.

Recovery of the sulphurous anhydride in liquid form accompanied by residual chlorine takes place in the second separator 15. Thus, according to the invention a stock of liquid $SO_2$ is available in an intermediate receptacle 16, from where a part of this compound passes via 17 to the cooling means 7 for the reactor 6 and another part passes via 19 and is vapourised in 20 to enter via the duct 19' into the inlet to the mixer 4. Thus the excess of $SO_2$ employed into the inlet to the mixer 4. Thus the excess of $SO_2$ employed according to the invention is continuously recycled, partly in the liquid state for cooling the reaction mixture in 6 and partly in the gaseous state to join the initial mixture in 4 and 4'.

As can thus be seen, the $SO_2$ recycled does not in practice contain residual hydracid, in particular HCl, because of the good separation capacity of the column 15. As regards the $SO_2$ dissolved in the liquid reaction product, this can be released on leaving 13 and recovered by the conduit 23.

EXAMPLE 1

The process and the apparatus according to the invention have been used by way of example for the preparation of sulphonyl methane chloride, $CH_3SO_2Cl$. In a reactor 6 of 6.5 liters capacity, containing a 15 watt mercury vapour lamp placed axially, the preparation as follows has been carried out.

The gaseous mixture prepared in 4 contains per 1 mole of $CH_4$, 6.25 moles of $SO_2$ and 0.83 mole of $Cl_2$. The hourly input of this feed gas is 250 liters normal per hour. The pressure in the reactor is adjusted to 4 bars above atmospheric. The temperature is regulated to $60°\pm2°$ C. by the injection of liquid $SO_2$ by means of the baffle 7; thus 220 g of $SO_2$ per hour are introduced.

In the receptacle 13, there is recovered per hour 125 g of crude sulphonyl methane chloride after cooling. At atmospheric pressure and the ambient temperature, this product has the following composition:

| | |
|---|---|
| $CH_3SO_2Cl$ | 75% |
| $SO_2$ | 20 |
| $CH_3Cl$ | 1.6 |
| $CH_2Cl_2$ | 1.2 |
| $CHCl_3$ | 1.2 |
| Heavy products | 1 |

The gaseous effluent which arrives via 14 in the second separator 15 has the composition by volume:

| | |
|---|---|
| $SO_2$ | 80% |
| HCl | 14 |
| $Cl_2$ | 1.2 |
| $CH_4$ | 2.9 |
| $CH_3Cl$ | 1.9 |

In order to recover the $SO_2$ in the liquid state under 4 bars relative pressure, the temperature in the separator 15 is maintained below 32° C.

The amount of $CH_4$ at the outlet 21 from the separator 15 is 7.16 normal liters per hour as against 29.4 introduced at 1; the conversion of the methane thus amounts to 76%. For the chlorine, the conversion is 88%. The results of this test show yields and selectivities as follows for the sulphonyl methane chloride produced:

| | | |
|---|---|---|
| for the methane | 62.3 | 82.4 |
| for the chlorine | 75.2 | 85.5 |

EXAMPLE 2

Preparation of sulphonyl ethane chloride

The process and apparatus described above have been used for the preparation of sulphonyl ethane chloride, $CH_3CH_2SO_2Cl$.

As the halogenation of an alkane is always more rapid if the latter has a symmetrical structure, ethane chlorinates more rapidly than methane and it is more sensitive to high concentrations of chlorine. This is why in the present example the gaseous mixture used is more diluted with $SO_2$ than in Example 1; for 1 mole of $C_2H_6$, it contains 12.5 moles of $SO_2$ and 0.83 mole of $Cl_2$. The hourly input of feed gas is 327 normal liters per hour.

The pressure in the reactor is fixed at 4 bars above the atmospheric pressure. To limit halogenations, it has been confirmed that a temperature of 40±5° C. is preferable. Liquid $SO_2$ is introduced by means of the baffle 7 to adjust the temperature; the quantity so injected is 165 g $SO_2$ per hour.

In the receptacle 13, there is recovered per hour 113.8 g of crude sulphonyl ethane chloride again after cooling. At atmospheric pressure and ambient temperature, this product has the following composition:

| | |
|---|---|
| $CH_3CH_2SO_2Cl$ | 75% |
| $SO_2$ | 20% |
| various halogenated products | 5% |

The gaseous effluent which arrives in the second separator 15 has the composition by volume:

| | |
|---|---|
| $SO_2$ | 88.4% |
| HCl | 4.6% |
| $Cl_2$ | 0.5% |
| $C_2H_6$ | 2.0% |
| chlorinated substances | 4.5% |

The temperature in the separator 15 is maintained below 32° C.

The amount of $C_2H_6$ at the outlet 21 from the separator 15 is 7.0 normal liters per hour as against 24.42 introduced at 1; the conversion of the ethane thus amounts to 71.3%. For the chlorine, the conversion is 91%. The results of this test give the following yield and selectivity of ethane sulphochloride.

| | Yield % | Selectivity % |
|---|---|---|
| for the ethane | 61% | 85% |
| for the chlorine | 73% | 80% |

The process is equally well adapted to the synthesis of the sulphochlorinated isomers of propane and butane. Two isomers are thus produced of each of the monosulphochlorides derived from these alkanes.

EXAMPLE 3

Preparation of propane sulphochloride

The gaseous mixture has a molar composition identical to that of Example 2. The hourly rate of feed is 327 normal liters per hour. The pressure is fixed at 6 bars above atmospheric pressure and the temperature at 50° C. To maintain the temperature, 200 g of liquid $SO_2$ per hour are introduced.

In the receptacle 13 there is recovered per hour 127.4 g of crude sulphonyl propane chloride after cooling. At atmospheric pressure and the ambient temperature, this product contains 85% by weight of a mixture of the two sulphochlorinated isomers of propane, namely 108.3 g.

The yield of the two isomers is the following:

$$CH_3-CH_2-CH_2-SO_2Cl: 71.4 \text{ g } (66\%)$$

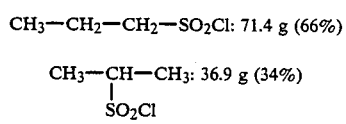

or substantially ⅔ of the 1-isomer for ⅓ of the 2-isomer.

These figures were obtained by chromatographic analysis and nuclear magnetic resonance studies. The preparation has given a yield of:
70% with respect to propane
84% with respect to chlorine for the two isomers together.

The other products formed are mono and polychlorinated isomers of propane.

EXAMPLE 4

Preparation of butane sulphochloride

The molar composition of the gaseous mixture at the inlet to the reactor is that of Examples 2 and 3, while the rate is 327 normal liters per hour. In contrast, to be certain of reacting the reactants in the vapour form, the total pressure is 5 bars and the temperature is 60° C. 150 g of liquid $SO_2$ per hour is sufficient to maintain the temperature at the desired level.

The crude production of the two sulphochlorinated isomers of butane is 135 g/h. The product is pure to about 85%, which gives a production of 114.7 g/h divided into:

CH₃—CH₂—CH₂—CH₂—SO₂Cl: 64.9 (57%)

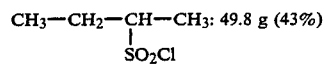
CH₃—CH₂—CH—CH₃: 49.8 g (43%)
          |
         SO₂Cl

The overall yield is 81% with respect to chlorine and 67.24% with respect to butane.

EXAMPLE 5

Preparation of sulphonyl methane chloride $CH_3SO_2Cl$ (designated by the abbreviation SMC)

Operation is as in Example 1 but under an absolute pressure of 10 bars and at a temperature of 50° C. in the reactor.

The gaseous mixture used contains per mole of $CH_4$ 5.41 moles of $SO_2$ and 0.71 moles of $Cl_2$, for an hourly input of 233. The partial pressure of $SO_2$ in the reactor is 7.6 Nl/h bars.

In the receptacle 13, maintained at a temperature of 120° C., there is recovered per hour 122 of a mixture containing SMC, halogenated derivatives of methane and dissolved $SO_2$ according to the following composition:

| | |
|---|---|
| —CH₃SO₂Cl | 73.3% |
| SO₂ | 23.3% |
| CH₃Cl | — |
| CH₂Cl₂ | 1.03% |
| —CHCl₃ | 0.96% |
| —CCl₄ | 0.25% |
| Heavy products | 1.15% |

The gaseous effluent which arrives via 14 in the second separator 15 has the composition by volume:

| | |
|---|---|
| —SO₂ | 85.1% |
| —HCl | 8.34% |
| —Cl₂ | 0.97% |
| —CH₄ | 4.72% |
| —CH₃Cl and others | 0.87% |

The $SO_2$ is recovered after cooling at 6 bars as in Example 1.

The conversion of the methane amounts to 63%. For the chlorine, the conversion is 90%. The results of this test give the yields and selectivities below for the sulphonyl methane chloride produced:

| | Yield % | Selectivity % |
|---|---|---|
| for the methane | 54 | 86 |
| for the chlorine | 76 | 85.2 |

EXAMPLE 6

In this example, the total pressure is 10 bars absolute and the gaseous mixture contains per mole of $CH_4$ 14.7 moles of $SO_2$ and 0.7 mole of $Cl_2$; the partial pressure of $SO_2$ is thus 9 bars. Hourly rate 536.2 Nl/h. There is recovered per hour 110.6 g of crude SMC of the composition:

| | |
|---|---|
| CH₃SO₂Cl | 77% |
| SO₂ | 21.51% |
| CH₂Cl₂ | 0.61% |
| CHCl₃ | 0.87% |

The gaseous effluent which arrives in the second separator:

| | |
|---|---|
| SO₂ | 94.9% |
| HCl | 3.2% |
| Cl₂ | 0.8% |
| CH₄ | 0.9% |
| CH₃Cl | 0.025% |
| Others | 0.17% |

The results of this test are the following, with a conversion of chlorine of 81%:

| | Yield % | Selectivity |
|---|---|---|
| for the methane | 51 | 85 |
| for the chlorine | 73 | 90 |

EXAMPLE 7

The same general conditions are used as in Example 5, but under a total pressure of 15 bars; partial pressure of $SO_2$ is 11.4 bars. The temperature is maintained at 65° C. by the injection of 200 grams per hour of liquid $SO_2$. There is recovered per hour at 13 154 g of crude SMC of the following composition:

| | |
|---|---|
| CH₃SO₂Cl | 63.1% |
| SO₂ | 35.2% |
| CH₂Cl₂ | 0.74% |
| CHCl₃ | 0.51% |

In the gaseous effluent, which arrives via 14 in the second separator, there are:

| | |
|---|---|
| SO₂ | 85.4% |
| HCl | 8.3% |
| Cl₂ | 0.9% |
| CH₄ | 5.1% |
| CH₃Cl | 0.03% |
| Others | 0.25% |

EXAMPLE 8

The operations of Example 1 are repeated under the following conditions:
4.22 moles $SO_2$ and 0.73 mole $Cl_2$ per mole of $CH_4$; Absolute pressure 10 bars, temperature 50°±2° C.
Gas input 250N liters per hour.

There was recovered 183.6 g of liquid per hour in the receptacle 13.

The temperature in the separator 15 is maintained below 38° C. and the pressure at 7 bars, so that the $SO_2$ remains liquid. The conversion of $CH_4$ is 76% and that of $Cl_2$ 86%.

| | |
|---|---|
| Yield | over CH₄ 63%, over Cl₂ 75%; |
| Selectivity | over CH₄ 83% over Cl₂ 87%. |

EXAMPLE 9

Example 8 was repeated but using a pressure of 1.6 bars at 50° C. The yields are then 40% over $CH_4$ and 47.6% over $Cl_2$ and the corresponding selectivities are respectively 52.7% and 55.2%.

Summary of Examples 1 and 5 to 9

For comparison purposes, the results of several of the Examples are set out below. P designates the absolute pressure. $P_{SO_2}$ designates the partial pressure of $SO_2$ in the gaseous mixture undergoing reaction.

|  | Example No. | | | | | |
| --- | --- | --- | --- | --- | --- | --- |
|  | 1 | 5 | 6 | 7 | 8 | 9 |
| P total (reactor) | 5 | 10 | 10 | 15 | 10 | 1.6 |
| $P_{SO_2}$ (reactor) | 4.8 | 7.6 | 9 | 11.4 | 7.1 | 1.4 |
| Temperature °C. | 60° | 60° | 60° | 65° | 50° | 50° |
| $SO_2/CH_4$ molar | 6.2 | 5.4 | 14.7 | 5.4 | 4.2 | 4.2 |
| Yield of $CH_3$ % | 62.3 | 54 | 51 | 68 | 63 | 40 |
| Selectivity of $CH_4$ % | 82.4 | 86 | 85 | 94 | 83 | 52.7 |
| Selectivity of $Cl_2$ % | 85.5 | 85.2 | 90 | 90 | 87 | 55.2 |

It can be confirmed that the selectivity and yield as to $CH_4$ of sulphonyl methane chloride increases with the pressure of the gaseous mixture in the reactor; thus from 82.4% for 5 bars (Example 1), the selectivity reaches 94% with 15 bars (Example 7). It is preferable that the number of moles of $SO_2$ present per mole of $CH_4$ is of the order of 5 to 7, because too high a number, e.g. about 15 (Example 6), leads to somewhat reduced yields and selectivities.

It is also to be noted that the more the pressure is elevated the better is the elimination of HCl in the separator 15.

We claim:

1. Process of preparation of sulphonyl alkane halides by the reaction between an alkane, sulphur dioxide and a halogen, in the presence of ultraviolet light in the gaseous phase, characterised in that the gaseous mixture of the reactants contains at least four moles of $SO_2$ per mole of hydrocarbon and in that the temperature of the reaction zone is regulated by the injection of liquid $SO_2$ into the reacting gaseous mixture.

2. Process according to claim 1, characterised in that the reaction takes place at a temperature from 10° to 90° C. under a pressure from 0.1 to 30 bars above atmospheric, such that the reacting mixture remains gaseous.

3. Process according to claim 2, characterised in that the temperature is in the range from 30° to 70° C. and the pressure is from 7 to 15 bars above atmospheric.

4. Process according to claim 1, in which the alkane is methane, the temperature being 50° to 70° C.

5. Process according to claim 1, characterised in that the reacting mixture contains per mole of methane 4 to 8 moles of $SO_2$ and 0.6 to 1 mole of $Cl_2$.

6. Process according to claim 5, characterised in that the proportions per mole of methane are 5 to 7 moles $SO_2$ and 0.7 to 0.9 mole $Cl_2$.

7. Process for the preparation of sulphonyl alkane halides which comprises reacting gaseous alkane, gaseous sulfur dioxide and gaseous halogen in a reaction zone in the presence of ultraviolet light at a temperature from 10° to 90° C. under a pressure of from 0.1 to 30 bars above atmospheric such that the resulting mixture remains gaseous and regulating the temperature of said reaction zone by injecting liquid $SO_2$ therein.

8. Process according to claim 7 in which the temperature is in the range from 30° to 70° C. and the pressure is from 7 to 15 bars above atmospheric.

9. Process according to claim 8 in which the alkane is methane, the temperature is 50° to 70° C., the amount of $SO_2$ is 4 to 8 mols per mol of methane and the amount of chlorine is 0.6 to 1 mol per mol of methane.

10. Process according to claim 9 in which the amount of $SO_2$ is 5 to 7 mols per mol of methane and the amount of chlorine is 0.7 to 0.9 mols per mol of methane.

11. Process according to claim 7 in which the alkane contains at least two carbon atoms and the amount of $SO_2$ is 7 to 14 mols per mol of alkane and the amount of chlorine is 0.6 to 1 mol of alkane.

12. Process according to claim 11 in which the amount of $SO_2$ is 10 to 13 mols per mol of alkane and the amount of chlorine is 0.7 to 0.9 mols per mol of alkane.

13. Process according to claim 7 wherein the alkane has 1–4 carbon atoms.

* * * * *